(12) United States Patent
Wang et al.

(10) Patent No.: US 11,952,388 B2
(45) Date of Patent: Apr. 9, 2024

(54) CRYSTAL FORM OF TRI-CYCLE COMPOUND AND APPLICATION THEREOF

(71) Applicant: FUJIAN AKEYLINK BIOTECHNOLOGY CO., LTD., Fujian (CN)

(72) Inventors: Jing Wang, Shanghai (CN); Zhigan Jiang, Shanghai (CN); Haiying He, Shanghai (CN); Yaxun Yang, Shanghai (CN)

(73) Assignee: Fujian Akeylink Biotechnology Co., Ltd., Fujian (CN)

(*) Notice: Subject to any disclaimer, the term of this patent is extended or adjusted under 35 U.S.C. 154(b) by 706 days.

(21) Appl. No.: 17/267,022

(22) PCT Filed: Aug. 23, 2019

(86) PCT No.: PCT/CN2019/102183
§ 371 (c)(1),
(2) Date: Feb. 9, 2021

(87) PCT Pub. No.: WO2020/038456
PCT Pub. Date: Feb. 27, 2020

(65) Prior Publication Data
US 2021/0230188 A1    Jul. 29, 2021

(30) Foreign Application Priority Data
Aug. 23, 2018   (CN) .......................... 201810969006.8

(51) Int. Cl.
*C07D 513/04* (2006.01)
*A61P 31/20* (2006.01)

(52) U.S. Cl.
CPC ............ *C07D 513/04* (2013.01); *A61P 31/20* (2018.01); *C07B 2200/13* (2013.01)

(58) Field of Classification Search
CPC ..... C07D 513/04; C07D 519/00; A61P 31/20; A61P 31/14; C07B 2200/13
See application file for complete search history.

(56) References Cited

U.S. PATENT DOCUMENTS 10,183,936 B2 *   1/2019   Turner, Jr. ........... C07D 243/38
11,053,260 B2 *   7/2021   He ....................... C07D 519/00
(Continued)

FOREIGN PATENT DOCUMENTS

RU         2537549 C2      1/2015

OTHER PUBLICATIONS

Mar. 22, 2022 Japanese Office Action issued in Application No. 2021510079.
(Continued)

*Primary Examiner* — Eric Olson
*Assistant Examiner* — Benjamin M Brandsen
(74) *Attorney, Agent, or Firm* — Houston Beshining Law Office PLLC; Liangang Ye

(57) ABSTRACT

Disclosed are crystal form A and crystal form B of a compound represented by formula (I), and application thereof in the preparation of medicaments for treating HBV-related diseases.

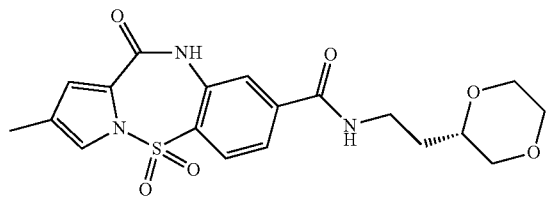

(I)

16 Claims, 4 Drawing Sheets
Specification includes a Sequence Listing.

(56) References Cited

U.S. PATENT DOCUMENTS

| | | |
|---|---|---|
| 2010/0240655 A1 | 9/2010 | Zhang |
| 2012/0282221 A1 | 11/2012 | Siegfried |
| 2017/0015658 A1 | 1/2017 | Turner, Jr. et al. |
| 2018/0319819 A1 | 11/2018 | Yogo et al. |
| 2020/0247819 A1 | 8/2020 | He et al. |
| 2023/0190768 A1* | 6/2023 | Wu .................... A61K 31/5365 514/211.02 |

OTHER PUBLICATIONS

Nov. 26, 2019 International Search Report issued in International Patent Application No. PCT/CN2019/102183.
Nov. 26, 2019 Written Opinion of the International Searching Authority issued in International Patent Application No. PCT/CN2019/102183.
Apr. 21, 2021 Taiwan Office Action issued in Taiwan Patent Application No. 108130314.
Priority application CN201810969006.8.
Dec. 13, 2021 The First Office Action issued in Russian application No. 2021105946.
Dec. 24, 2021 First Office Action issued in Chinese application No. 2019800536984.
Nov. 25, 2021 EESR issued in European application No. 19853095.8.
Nov. 16, 2021 First Office Action issued in Japanese application No. 2021-510079.
Dec. 2, 2021 First Office Action issued in Korean application No. 10-2021-7008378.

* cited by examiner

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Forward primer sequence

<400> SEQUENCE: 1
gtgtctgcgg cgttttatca                                              20

<210> SEQ ID NO 2
<211> LENGTH: 21
<212> TYPE: DNA
<213> ORGANISM: Artificial Sequence
<220> FEATURE:
<223> OTHER INFORMATION: Reverse primer sequence

<400> SEQUENCE: 2
gacaaacggg caacatacct t                                            21

<210> SEQ ID NO 3
<211> LENGTH: 28
<212> TYPE: DNA
<213> ORGANISM: Artificial Sequence
<220> FEATURE:
<223> OTHER INFORMATION: Nucleotide sequence of probe

<400> SEQUENCE: 3
cctctkcatc ctgctgctat gcctcatc                                     28

CRYSTAL FORM OF TRI-CYCLE COMPOUND AND APPLICATION THEREOF

The Sequence Listing is submitted concurrently with the specification as an ASCII formatted text file via EFS-Web, with a file name of "P21410097US-2-SEQ", a creation date of Jan. 21, 2021, and a size of 868 bytes. The Sequence Listing filed via EFS-Web is part of the specification and is incorporated in its entirety by reference herein.

This application is a National Stage of International Application No. PCT/CN2019/102183, filed on Aug. 23, 2019, which claims priority of Chinese patent application CN2018109690068, filed on Aug. 23, 2018, the contents of which are incorporated herein by its entirety.

TECHNICAL FIELD

The present disclosure relates to crystal form A and crystal form B of a compound represented by formula (I), and application thereof in the preparation of a medicament for treating HBV-related diseases.

BACKGROUND ARTS

Hepatitis B is an inflammatory response caused by the invasion of hepatitis B virus, which can lead to a series of problems such as pain in the liver region, hepatosplenomegaly, liver fibrosis, and cirrhosis and even liver cancer in severe cases. Statistically, there are 350-400 million hepatitis B virus carriers around the world, ⅓ of which are in China, and the death toll caused by hepatitis B in China is up to 500,000 every year.

There are no specific drugs for treating Hepatitis B worldwide at this stage. The first line drugs for treating Hepatitis B in China are mainly nucleoside drugs, interferons and traditional Chinese medicine. However, there are problems such as high cost and susceptibility to relapse, and hence it is imperative to develop a new type of anti-hepatic drug.

WO2008154817A1 discloses the structure of GLS4 as follows:

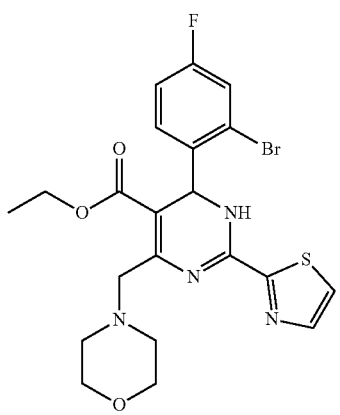

GLS4

Content of the Present Invention

The present disclosure provides a crystal form A of a compound represented by formula (I) having a X-ray powder diffraction (XRPD) pattern comprising characteristic diffraction peaks with the following angles of 2θ: 5.56±0.2°, 15.56±0.2° and 16.17±0.2°,

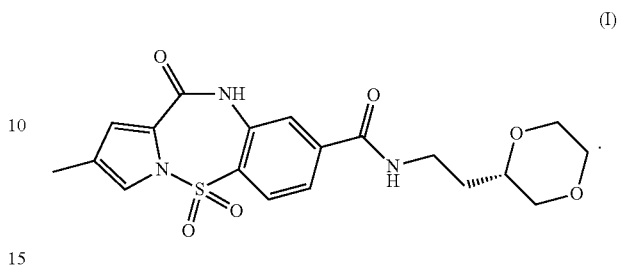

(I)

In some embodiments of the present disclosure, the X-ray powder diffraction pattern of the crystal form A as defined above comprises characteristic diffraction peaks with the following angles of 2θ: 5.56±0.2°, 10.84±0.2°, 15.56±0.2°, 16.17±0.2°, 22.14±0.2°, 22.70±0.2°, 27.76±0.2° and 28.44±0.2°.

In some embodiments of the present disclosure, the XRPD pattern of the crystal form A as defined above is shown in FIG. 1.

In some embodiments of the present disclosure, the analysis data of the XRPD pattern of the crystal form A as defined above is shown in Table 1.

TABLE 1

Analytical data of the XRPD pattern of the crystal form A

| No. | 2θ Angle (°) | d-spacing (Å) | Intensity | Relative intensity (%) | Area | Relative area (%) |
|---|---|---|---|---|---|---|
| 1 | 5.559 | 15.8847 | 9479 | 100 | 125596 | 100 |
| 2 | 10.837 | 8.1568 | 212 | 2.2 | 3329 | 2.7 |
| 3 | 11.121 | 7.9493 | 323 | 3.4 | 8739 | 7 |
| 4 | 11.335 | 7.7998 | 413 | 4.4 | 8593 | 6.8 |
| 5 | 14.924 | 5.9312 | 272 | 2.9 | 1960 | 1.6 |
| 6 | 15.559 | 5.6904 | 820 | 8.7 | 8717 | 6.9 |
| 7 | 16.167 | 5.4778 | 909 | 9.6 | 8321 | 6.6 |
| 8 | 18.611 | 4.7638 | 144 | 1.5 | 2007 | 1.6 |
| 9 | 18.968 | 4.6749 | 162 | 1.7 | 1986 | 1.6 |
| 10 | 22.143 | 4.0112 | 391 | 4.1 | 4717 | 3.8 |
| 11 | 22.698 | 3.9144 | 577 | 6.1 | 9392 | 7.5 |
| 12 | 25.299 | 3.5175 | 175 | 1.8 | 2183 | 1.7 |
| 13 | 26.82 | 3.3213 | 106 | 1.1 | 2409 | 1.9 |
| 14 | 27.147 | 3.282 | 118 | 1.2 | 3302 | 2.6 |
| 15 | 27.765 | 3.2104 | 464 | 4.9 | 4055 | 3.2 |
| 16 | 28.437 | 3.136 | 425 | 4.5 | 4436 | 3.5 |

In some embodiments of the present disclosure, the crystal form A as defined above exhibits an endothermic peak with an onset of 229.95° C. as measured by differential scanning calorimetry curve (DSC).

In some embodiments of the present disclosure, the DSC of the crystal form A as defined above is shown in FIG. 2.

In some embodiments of the present disclosure, the crystal form A as defined above has a thermogravimetric analysis (TGA) curve with a weight loss of 0.3382% at 62±3° C. and a weight loss of 0.8753% at 230±3° C.

In some embodiments of the present disclosure, the TGA of the crystal form A as defined above is shown in FIG. 3.

The present disclosure also provides a crystal form B of a compound represented by formula (I) having an X-ray powder diffraction pattern comprising characteristic diffraction peaks with the following angles of 2θ: 12.70±0.2°, 15.64±0.2° and 23.03±0.2°.

In some embodiments of the present disclosure, the X-ray powder diffraction pattern of the crystal form B as defined above comprises characteristic diffraction peaks with the following angles of 2θ: 9.56±0.2°, 12.70±0.2°, 14.41±0.2°, 15.64±0.2°, 19.70±0.2°, 23.03±0.2°, 23.98±0.2° and 27.65±0.2°.

In some embodiments of the present disclosure, the XRPD pattern of the crystal form B as defined above is shown in FIG. 4.

In some embodiments of the present disclosure, the analysis data of the XRPD pattern of the crystal form B as defined above is shown in Table 2.

TABLE 2

Analytical data of the XRPD pattern of the crystal form B

| No. | 2θ Angle (°) | d-spacing (Å) | Intensity | Relative intensity (%) | Area | Relative area (%) |
|---|---|---|---|---|---|---|
| 1 | 9.563 | 9.2407 | 548 | 7.6 | 4827 | 6.9 |
| 2 | 12.206 | 7.2452 | 169 | 2.4 | 2005 | 2.9 |
| 3 | 12.696 | 6.9666 | 1456 | 20.3 | 13463 | 19.3 |
| 4 | 14.414 | 6.1399 | 909 | 12.7 | 8228 | 11.8 |
| 5 | 15.638 | 5.6621 | 7183 | 100 | 69797 | 100 |
| 6 | 17.194 | 5.153 | 728 | 10.1 | 6918 | 9.9 |
| 7 | 17.47 | 5.072 | 519 | 7.2 | 5752 | 8.2 |
| 8 | 18.675 | 4.7474 | 158 | 2.2 | 1339 | 1.9 |
| 9 | 19.009 | 4.6648 | 244 | 3.4 | 2337 | 3.3 |
| 10 | 19.698 | 4.5032 | 548 | 7.6 | 4198 | 6 |
| 11 | 20.368 | 4.3566 | 306 | 4.3 | 2729 | 3.9 |
| 12 | 22.125 | 4.0144 | 374 | 5.2 | 3126 | 4.5 |
| 13 | 22.636 | 3.9249 | 144 | 2 | 2929 | 4.2 |
| 14 | 23.03 | 3.8586 | 2928 | 40.8 | 29432 | 42.2 |
| 15 | 23.624 | 3.763 | 240 | 3.3 | 1652 | 2.4 |
| 16 | 23.98 | 3.7079 | 775 | 10.8 | 6496 | 9.3 |
| 17 | 24.826 | 3.5833 | 212 | 3 | 2080 | 3 |
| 18 | 25.618 | 3.4744 | 222 | 3.1 | 4391 | 6.3 |
| 19 | 25.951 | 3.4306 | 125 | 1.7 | 1238 | 1.8 |
| 20 | 26.482 | 3.363 | 214 | 3 | 2557 | 3.7 |
| 21 | 26.824 | 3.3209 | 310 | 4.3 | 3168 | 4.5 |
| 22 | 27.646 | 3.224 | 1137 | 15.8 | 10294 | 14.7 |
| 23 | 28.633 | 3.1151 | 245 | 3.4 | 2126 | 3 |
| 24 | 29.029 | 3.0735 | 276 | 3.8 | 3120 | 4.5 |
| 25 | 29.699 | 3.0056 | 351 | 4.9 | 4634 | 6.6 |
| 26 | 30.386 | 2.9392 | 108 | 1.5 | 1086 | 1.6 |
| 27 | 31.789 | 2.8126 | 151 | 2.1 | 3160 | 4.5 |
| 28 | 32.99 | 2.7129 | 135 | 1.9 | 2222 | 3.2 |
| 29 | 33.738 | 2.6544 | 113 | 1.6 | 1322 | 1.9 |
| 30 | 34.607 | 2.5898 | 103 | 1.4 | 1580 | 2.3 |
| 31 | 35.416 | 2.5324 | 209 | 2.9 | 2355 | 3.4 |
| 32 | 35.946 | 2.4963 | 113 | 1.6 | 1987 | 2.8 |
| 33 | 38.85 | 2.3161 | 93 | 1.3 | 1304 | 1.9 |

In some embodiments of the present disclosure, the crystal form B as defined above exhibits an endothermic peak with an onset of 233.59° C. as measured by differential scanning calorimetry curve.

In some embodiments of the present disclosure, the DSC of the crystal form B as defined above is shown in FIG. 5.

In some embodiments of the present disclosure, the crystal form B as defined above has a thermogravimetric analysis curve with a weight loss of 0.04890% at 120±3° C.

In some embodiments of the present disclosure, the TGA of the crystal form B as defined above is shown in FIG. 6.

The present disclosure also provides a use of the crystal form A or the crystal form B as defined above in the preparation of a medicament for treating HBV-related diseases.

Technical Effects

The crystal form A and the crystal form B of the compound represented by formula (I) of the present invention are stable and less affected by heat and humidity with good in vivo administration efficacy, and are promising in preparing medicaments.

Definitions and Explanations

Unless otherwise indicated, the following terms and phrases used in this document are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known for those skilled in the art. Preferred embodiments include, but are not limited to the embodiments of the present disclosure.

The chemical reactions in the embodiments of the present disclosure are carried out in a suitable solvent, and the solvent should be suitable for the chemical change, and the required reagents and materials of the present disclosure. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

Solvents used in the present disclosure are commercially available. The present disclosure employs the following abbreviations: EtOH stands for ethanol; MeOH stands for methanol; TFA stands for trifluoroacetic acid; TsOH stands for p-toluenesulfonic acid; mp stands for melting point; EtSO$_3$H stands for ethanesulfonic acid; MeSO$_3$H stands for methanesulfonic acid; THF stands for tetrahydrofuran; EtOAc stands for ethyl acetate; THF stands for tetrahydrofuran; EA stands for ethyl acetate; DMAP stands for 4-dimethylaminopyridine; DCM stands for dichloromethane; DIPEA stands for N,N-diisopropylethylamine.

X-Ray Powder Diffractometer (XRPD)

About 10-20 mg of sample was used for XRPD detection.
The detailed XRPD parameters are as follows:
X-ray tube: Cu, kα, (λ=1.54056 Å).
X-ray tube voltage: 40 kV, X-ray tube current: 40 mA
Divergence slit: 0.60 mm
Detector slit: 10.50 mm
Anti-scattering slit: 7.10 mm
Scanning range: 3-40 deg or 4-40 deg
Step size: 0.02 deg
Step time: 0.12 second
Rotation speed of sample tray: 15 rpm Differential Scanning Calorimeter (DSC)

0.5-1 mg of sample was placed in a DSC aluminum crucible for testing by increasing the temperature of sample from 30° C. to 300° C. at a rate of 10° C./min under 50 mL/min N$_2$.

Thermal Gravimetric Analyzer (TGA)

2-5 mg of sample was placed in a TGA platinum crucible for testing, and heated at a rate of 10° C./min under 25 mL/min $N_2$ to increase the temperature of sample from room temperature to 300° C. or to make the sample lose 20% of weight.

The Dynamic Vapor Sorption Analyzer (DVS)

Detection condition: 10-15 mg of the sample was placed in sample tray for DVS detection.

Detailed parameters of DVS are as follows:

Temperature: 25° C.

Equilibrium: dm/dt=0.01%/min: (shortest: 10 min, longest: 180 min)

Drying: 0% RH, 120 min

RH (%) gradient for testing: 10%

RH (%) gradient range for testing: 0%-90%-0%

| The followings are the criteria for evaluations: | |
|---|---|
| Scales for hygroscopicity | Hygroscopic weight gain* |
| Deliquescence | Absorbing sufficient water to form liquid |
| High hygroscopicity | ΔW % ≥ 15% |
| Medium hygroscopicity | 15% > ΔW % ≥ 2% |
| Low hygroscopicity | 2% > ΔW % ≥ 0.2% |
| No or almost no hygroscopicity | ΔW % < 0.2% |

Hygroscopic weight gain at 25° C./80% RH

DETAILED DESCRIPTION OF THE PREFERRED EMBODIMENT

Figure 1:
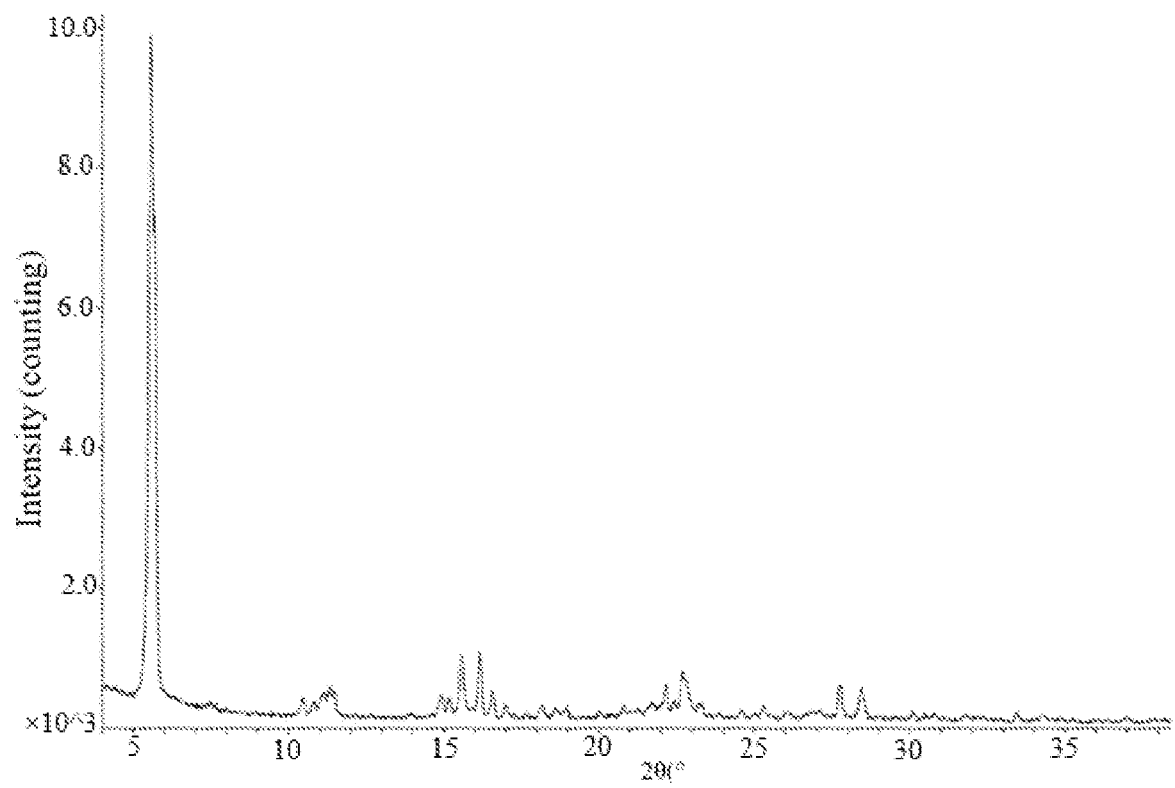
FIG. 1 is the XRPD pattern of Cu-Kα radiation of the crystal form A of the compound represented by formula (I).

In order to better understand the contents of the present disclosure, the following embodiments further illustrate the present disclosure, but the present disclosure is not limited thereto.

Example 1 Preparation of the Compound Represented by Formula (I)

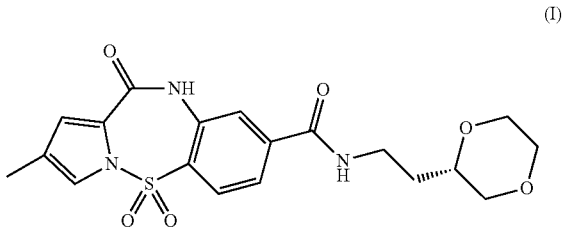 [SMILES: Cc1cc2n(c1)S(=O)(=O)c1ccc(C(=O)NCC[C@H]3COCCO3)cc1NC2=O]

Synthetic Route

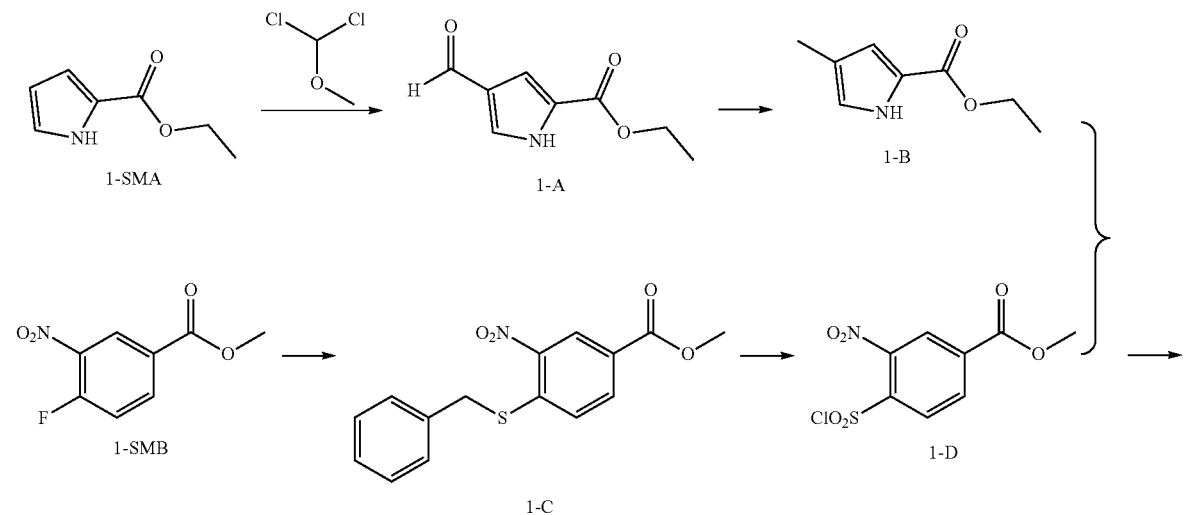

-continued

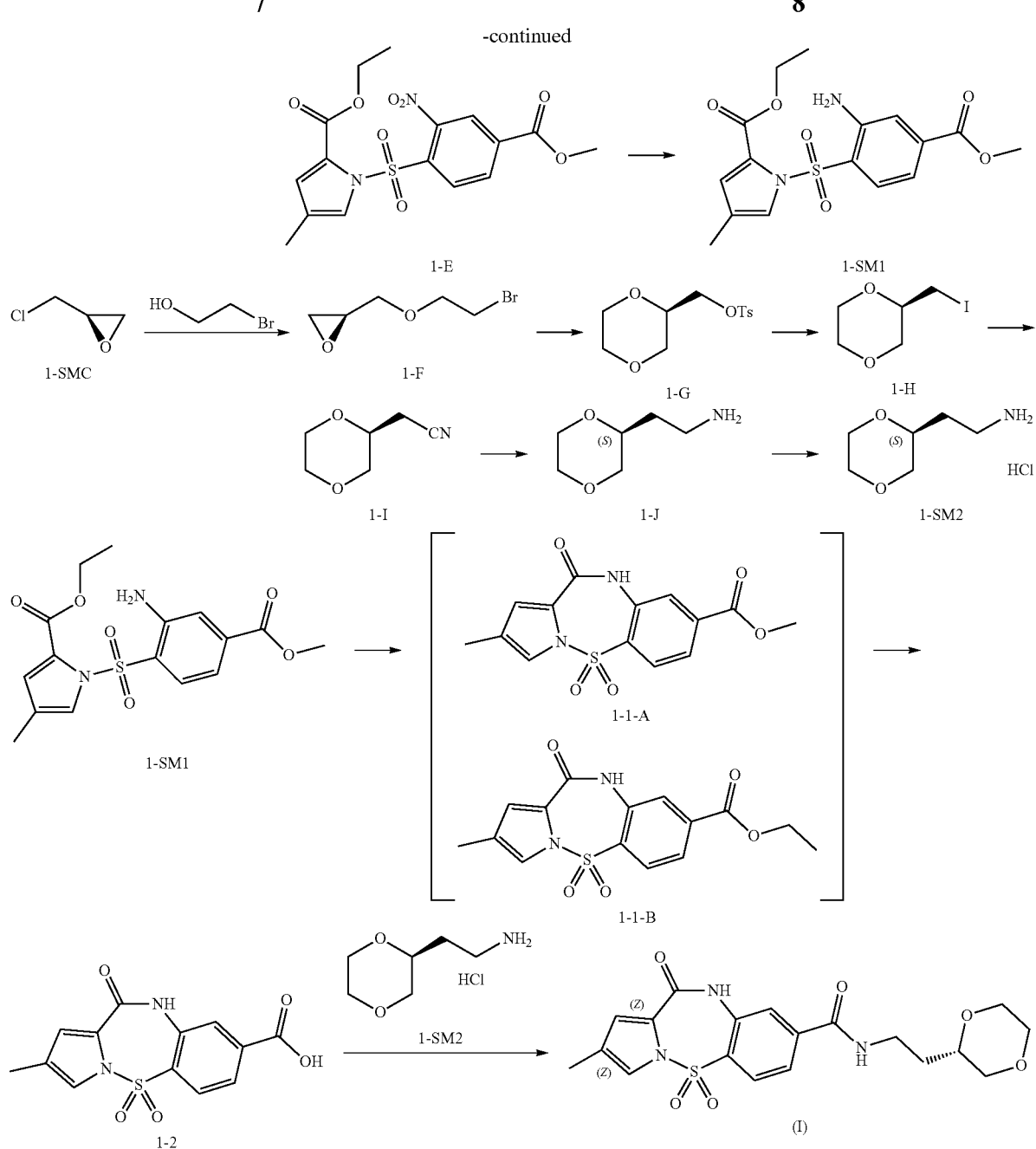

Step 1: Synthesis of Compound 1-A

Anhydrous dichloromethane (5 L) was added into a dry three-necked flask (10 L) and stirred, then compound 1-SMA (500.00 g) and nitromethane were added into the three-necked flask successively to obtain a mixture. The mixture was placed in a dry ice ethanol bath, and cooled to −10° C. The temperature was controlled between −10° C.-0° C. Aluminum trichloride (1.15 kg) was slowly added into the reaction flask and the temperature was controlled to less than −0° C. Next, α,α-dichlorodimethyl methyl ether (495.00 g) was slowly added into the reaction kettle to obtain a reaction solution, which was slowly heated to room temperature and stirred for 18 hours. TLC (PE:EA 3:1) monitoring revealed the disappearance of the raw material spot and the appearance of a new spot with high polarity. Potassium bisulfate solution (3 L) was slowly added dropwise to the extracted reaction solution to a concentration of 10%, stirred for 20 minutes while crushed ice was added to prevent overheating. The mixed solution was transferred to a 25 L separatory funnel and allowed to stand for stratification to separate the dichloromethane layer, and the aqueous phase was extracted with dichloromethane (2L*2). After washing with 10% potassium bisulfate solution (5 L*2), the organic phase was separated and dried with anhydrous sodium sulfate (1 kg). The organic phase was concentrated under reduced pressure to obtain compound 1-A as a dark-green solid.

$^1$H NMR (400 MHz, deuterated chloroform) δ=9.97 (br s, 1H), 9.87-9.82 (m, 1H), 7.58 (dd, J=1.5, 3.3 Hz, 1H), 7.36-7.29 (m, 1H), 4.37 (q, J=7.1 Hz, 2H), 1.38 (t, J=7.2 Hz, 3H).

Step 2: Synthesis of Compound 1-B p-toluenesulfonyl hydrazide (2.23 kg, 11.96 mol) was added into the THF (20 L) solution containing compound 1-A (2 kg, 11.96 mol). The solution was stirred at 20° C. for about 1 h. When the disappearance of the raw material was monitored by TLC, the reaction system was heated to 60° C., and sodium cyanoborohydride (902 g, 14.36 mol) was added in batches. After the addition, the reaction solution was heated to 70° C. and stirred for 3 h. After the heating was stopped and cooled down to room temperature, 5 L of water was added to quench the reaction, followed by removing most of the THF under reduced pressure, and the residue was extracted with a large amount of EA (1.5 L*3). The organic phases were pooled, washed with saturated sodium chloride and dried with anhydrous sodium sulfate. Then the organic phases were filtered, and the solvent was removed under reduced pressure. Finally, the crude product was column chromatographed to obtain compound 1-B as a pale-yellow solid.

Step 3: Synthesis of Compound 1-C

Methanol (32 L) was added into a 50 L jacketed kettle and stirred, then compound 1-SMB (4000.00 g) and diisopropylethylamine (5.25 L) was added successively, and the internal temperature was reduced to 5-10° C. Benzyl mercaptan (2490.00 g) was slowly added dropwise, and the internal temperature was maintained at 5-15° C. After the addition was complete, the cooling system was turned off to let the temperature rise naturally, and stirring was continued for 2.5 h. Next, stirring was stopped, the speed was adjusted to 100 rpm, and the reaction liquid was released and filtered through a desktop filter to obtain a filter cake. The filter cake was washed three times with water (5 L), followed by once with EtOH (3 L). The filter cake was filtered by suction filtration until it was no longer viscous, thereby obtaining compound 1-C as a pale-yellow solid.

Step 4: Synthesis of Compound 1-D

Dichloromethane (7.5 L) was added into a 50 L kettle and stirred, then compound 1-C (1500 g) was added. The internal temperature was reduced to 0-10° C., and HCl solution (6 M, 4.12 L) was added. The sodium hypochlorite solution (commercially available 8% solution, 23.0 kg) was added dropwise under 0-10° C. with the lid open. After dropwise addition, the cooling system was turned off and stirring was continued for about 17 hours with the lid open. Then sodium bisulfite was added (1000 g, 5 L aqueous solution), and starch potassium iodide test paper was used to detect if there is no oxidant remaining in the water phase. Next, stirring was stopped, the solution was allowed to stand for stratification. The dichloromethane layer was collected while the aqueous layer was extracted with dichloromethane (2.5 L), and the dichloromethane layers were pooled. The organic phase was dried with anhydrous sodium sulfate and filtered, then the solvent was removed under reduced pressure to obtain compound 1-D as a white solid.

$^1$H NMR (400 MHz, deuterated chloroform) δ=8.50-8.43 (m, 2H), 8.34 (d, J=8.2 Hz, 1H), 4.04 (s, 3H).

Step 5: Synthesis of Compound 1-E

Tetrahydrofuran (10 L) was added into a dry 50 L jacketed kettle and stirred, then compound 1-B (2000 g) was added. The internal temperature was reduced to 0-10° C. The temperature was maintained at 0-15° C. in about 1.5 hours, and potassium tert-butoxide (1 M THF solution, 15.67 L) was added. After addition, the temperature was raised to about 20° C. and the stirring was continued for 1 hour. Next, the temperature was reduced to 0-10° C., and the THF (10 L) solution containing compound 1-D (4380 g) was slowly added. After addition, the temperature was slowly raised to 15° C. and the stirring was continued for about 16 hours. Ethyl acetate (10 L) was added for extraction, and the organic phase was washed with saturated sodium chloride solution (10 L) twice. The aqueous phases were combined and extracted with EA (5 L), and the organic phases were combined. Finally, the solvent was removed from the organic phase under reduced pressure to obtain compound 1-E as a pale-yellow solid.

$^1$H NMR (400 MHz, DMSO-d$_6$) δ=8.55 (d, J=1.4 Hz, 1H), 8.37 (dd, J=1.5, 8.3 Hz, 1H), 7.91 (d, J=8.3 Hz, 1H), 7.60 (s, 1H), 7.13 (d, J=1.8 Hz, 1H), 4.02 (q, J=7.0 Hz, 2H), 3.93 (s, 3H), 2.10 (s, 3H), 1.08 (t, J=7.1 Hz, 3H).

Step 6: Synthesis of Compound 1-SM1

Compound 1-E (1000.0 g) was added into a dry 10 L three-necked flask and stirred, then glacial acetic acid (5 L) was added and the internal temperature of the reaction was controlled at 25-30° C. Iron powder (1 eq, 140.9 g) was slowly added. After stirring for 30 minutes, the second batch of iron powder (0.5 eq, 70.44 g) was slowly added. After continuing stirring for 30 minutes, the third batch of iron powder (0.5 eq, 70.44 g) was added. After another 30 min of stirring, the fourth batch of iron powder (0.5 eq, 70.44 g) was added, and the reaction continued to be stirred until the disappearance of raw material and the appearance of a new point with high polarity were monitored. Next, stirring was stopped, and the reaction solution was transferred to 25 L dispenser for liquid separation. 10 L of ethyl acetate was added to the solution, which was then washed with 5 L saturated sodium bisulfate aqueous solution twice. After the liquid separation, the aqueous phase was back-extracted with 5 L of ethyl acetate. The organic phases were then combined and washed with 10% NaOH aqueous solution until pH>8, and the organic phase was collected by liquid separation. The organic phase was concentrated under reduced pressure to obtain compound 1-SM1 as a white solid.

$^1$H NMR (400 MHz, DMSO-d$_6$) δ=7.79-7.71 (m, 2H), 7.50 (d, J=1.8 Hz, 1H), 7.14 (dd, J=1.7, 8.5 Hz, 1H), 6.96 (d, J=2.0 Hz, 1H), 6.42 (s, 2H), 4.11 (q, J=7.2 Hz, 2H), 3.84 (s, 3H), 2.04 (s, 3H), 1.16 (t, J=7.1 Hz, 3H).

Step 7: Synthesis of Compound 1-F

Toluene (12 L) was added to a dry 50 L jacketed kettle and stirred, then 2-bromoethanol (9930 g) was added, followed by boron trifluoride ether (268 g). The reaction was heated to 30-35° C. Compound 1-SMC (3500 g) was slowly added dropwise, and the addition was completed in about 1.5 hours. After addition, the internal temperature of the reaction was raised to about 55-65° C. and the temperature setting of heater was adjusted to 60° C. to keep the internal temperature at 55-65° C. for 1 hour. Then the internal temperature of the system was reduced to about 10° C., and sodium hydroxide aqueous solution (3783 g, water 17.5 L) at about 20° C. was slowly added into the reaction system while the internal temperature was maintained at 10-20° C. After the addition of NaOH solution, the temperature control of the heater was turned off, and the reaction continued to stir for about 16 h. Then the stirring was stop that the reaction solution was allowed to stand for stratification. The aqueous layer was extracted with 2-methyltetrahydrofuran (10 L) and the organic phases were combined, washed with water (10 L) and allowed to stand for stratification to collect organic phase. The organic phase was finally concentrated under reduced pressure to obtain compound 1-F as a colorless oil.

$^1$H NMR (400 MHz, deuterated chloroform) δ=3.87-3.71 (m, 4H), 3.66-3.59 (m, 3H), 3.42 (dd, J=6.0, 11.7 Hz, 1H), 3.20-3.13 (m, 1H), 2.79 (t, J=4.6 Hz, 1H), 2.65-2.59 (m, 1H).

Step 8: Synthesis of Compound 1-G

An aqueous solution of sodium hydroxide (3240 g, 15 L of water) was added into a 50 L jacketed kettle, compound 1-F (4430 g) was then added and the heating was turned on. After the reaction was heated to 90° C., the stirring was continued for 1 h. The cooling was turned on to reduce the reaction to about 15° C., then THF solution (6180 g, tetrahydrofuran 15 L) containing p-toluenesulfonyl chloride solution was added. The temperature control of the heater was turned off, and the reaction was further stirred at about 15° C. for about 16 h. Next, the stirring was stopped to let the reaction allowed to stand for stratification. The aqueous phase was extracted with 2-methyltetrahydrofuran (10 L), and the 2-methyltetrahydrofuran phase (there was white insoluble matter, which disappeared after the washing) was washed with water (5 L), and the organic phases were combined. DMAP (500 g) and triethylamine (2.5 L) were added to the organic phase, followed by stirring the organic phase for 30 minutes. Then the organic phase was washed with saturated sodium chloride solution (10 L) and allowed to stand for stratification, and the water phase was discarded. The organic phase was washed with potassium hydrogen sulfate solution (3800 g, 15 L of water) and saturated sodium chloride solution (5 L*twice) successively, and then allowed to stand for stratification, and the organic phase was collected. The organic phase was finally concentrated under reduced pressure to remove the solvent to obtain the crude product compound 1-G.

$^1$H NMR (400 MHz, deuterated chloroform) δ=7.77 (d, J=8.3 Hz, 2H), 7.34 (d, J=8.2 Hz, 2H), 4.03-3.91 (m, 2H), 3.80-3.49 (m, 8H), 3.33 (dd, J=9.9, 11.4 Hz, 1H), 2.43 (s, 3H).

Step 9: Synthesis of Compound 1-H

Acetone (30 L) was added into a clean 50 L jacketed kettle and stirred, then compound 1-G (4500 g) was added, followed by sodium iodide (6190 g). The heating was turned on, and after the reaction was heated to 75° C., the stirring was continued for 16 hours. After being cooled to room temperature, the reaction was filtered, and the filtrate was concentrated under reduced pressure at 50° C. Ethyl acetate (15 L) and water (10 L) were added to the concentrated crude product, and the mixture was stirred and then allowed to stand for stratification. The organic phase was washed with 0.5 M sodium thiosulfate (10 L). The aqueous phase and sodium thiosulfate solution were combined and extracted with EtOAc (5 L). The organic phases were combined and washed with saturated sodium chloride solution (10 L), then allowed to stand for stratification, and the organic phase was collected. The organic phase was finally concentrated under reduced pressure to remove the solvent to obtain the crude product compound 1-H.

$^1$H NMR (400 MHz, deuterated chloroform) δ=3.90-3.83 (m, 2H), 3.81-3.75 (m, 2H), 3.74-3.65 (m, 5H), 3.63-3.49 (m, 7H), 3.31-3.18 (m, 3H), 3.06-3.04 (m, 2H).

Step 10: Synthesis of Compound 1-I

DMSO (20 L) was added into a clean 50 L jacketed kettle and stirred, then compound 1-H (4700 g) was added and the temperature was raised to 35° C., followed by adding sodium cyanide (1010 g). The internal temperature of the reaction was raised to about 60° C. within 20 minutes, then the temperature was gradually reduced to 35° C., and the stirring was continued for about 16 hours. Sodium bicarbonate solution (2000 g sodium bicarbonate, 10 L of water) was added to the reaction system, which was then stirred for about 5 minutes. EtOAc:MeOH (20 L, 2 L) was added and the reaction system was further stirred for 2 minutes, followed by standing for about 1 hour. Next, the reaction system was partitioned and about 30 L of the lower layer solution was separated. The lower layer solution was extracted twice with EtOAc:MeOH (15 L:1.5 L for the first time, and 5 L:0.5 L for the second time). After the extraction, the upper organic phase and the upper layer of the remaining reaction liquid were combined, washed three times with saturated sodium chloride solution (10 L each), and allowed to stand for stratification. The aqueous phase was discarded while the organic phase was collected. Finally, the solvent was removed from the organic phase under reduced pressure, and the crude product was column chromatographed to obtain compound 1-I as a colorless oil.

$^1$H NMR (400 MHz, deuterated chloroform) δ=3.84-3.65 (m, 6H), 3.61-3.53 (m, 2H), 3.35 (t, J=10.5 Hz, 1H), 2.49-2.44 (m, 2H).

Step 11: Synthesis of Compound 1-J

Under the protection of argon, Raney nickel (10.00 g, 116.73 mmol) and EtOH (150 mL) were added into the dry hydrogenation flask, and then 1-I (20 g, 157.31 mmol,) and NH$_3$·H$_2$O (13.65 g, 97.36 mmol, 15.00 mL, 25% purity) were added, followed by replacement, and the reaction was stirred at 50 psi and 50° C. for 3.5 h. The reaction solution was filtered using diatomite, and the filtrate was concentrated under reduced pressure to obtain compound 1-J as a yellow oil.

$^1$H NMR (400 MHz, deuterated chloroform) δ=3.82-3.57 (m, 6H), 3.34-3.18 (m, 1H), 2.86-2.72 (m, 2H), 1.60-1.38 (m, 2H).

Step 12: Synthesis of Compound 1-SM2

1-J (800.00 g) was added into a 5 L three-necked flask and stirred, then ethyl acetate (800 mL) was added within 0.5 h, and 4M HCl/EtOAc (1.6 L) was slowly added dropwise till the pH of the system was smaller than 5 while the internal temperature was maintained at 5-15° C. Next, the cooling system was turned off, and the reaction was heated to room temperature and further stirred for 1 hour. After stopping the stirring, the reaction was filtered through a desktop filter to obtain a filter cake, which was then concentrated under reduced pressure (40-45° C.) to obtain a crude product. Acetonitrile (2 mL/g) was added to the preceding product and the mixture was slurried for 1 hour. After the slurried product was filtered, the filter cake was collected separately, and the organic solution was removed under reduced pressure to obtain a white solid compound 1-SM2.

$^1$H NMR (399 MHz, METHANOL-d$_4$) δ=3.88-3.72 (m, 5H), 3.67-3.59 (m, 1H), 3.36-3.31 (m, 1H), 3.14 (t, J=6.7 Hz, 2H), 1.87-1.67 (m, 2H).

Step 13: Synthesis of Compound 1-1-A and Compound 1-1-B

Toluene (20 L) was added into a dry 50 L jacketed kettle and stirred, then compound 1-SM1 (2500 g), and the internal temperature was raised to 30-35° C. The inert gas environment in the kettle was maintained by nitrogen purging. Then trimethylaluminum (3.0 L, the temperature in the kettle rises slowly with the addition of Al(CH$_3$)$_3$) was added dropwise. After addition, the nitrogen purging was turned off. The temperature was raised to 80-85° C. and the reaction was further stirred about 16 hours. Next, the cooling was turned on to reduce the temperature of the reaction to 20-30° C. Half of the reaction solution (about 12 L), to which EtOAc (10 L) was added, was transferred and mixed well. The mixed solution was added to 10% KHSO$_4$ solution (10 L) while stirring, stirred for 2 minutes and then allowed to stand for stratification. The organic layer was washed with 10% KHSO$_4$ solution (10 L), the water phases were combined and extracted twice with DCM (each 7.5 L). The other half of the reaction solution (about 12 L) was transferred out, which was treated in the same way as defined above. Then the organic phases were combined and concentrated under reduced pressure to obtain a crude product. Two times the volume of n-heptane was added and beaten for 1 hour to form a slurry. The slurry was filtered, and vacuum-dried for >12 hours at 40° C., P≤−0.1 MPa. A mixture of compound 1-1-A and compound 1-1-B was obtained as a white solid.

Step 14: Synthesis of Compound 1-2

Tetrahydrofuran (3840 mL) was added into a 10 L three-necked flask and stirred, and the mixture of compound 1-1-A and compound 1-1-B (480.00 g) was added slowly, then $H_2O$ (960 mL) solution of $LiOH \cdot H_2O$ (118.84 g) was added dropwise slowly. After addition, the temperature was raised to 60° C. and the reaction was stirred for 1 hour. Then concentrated HCl was added to the reaction solution to adjust the pH of the system to 2, and stop stirring. Next, the solution was left standing for liquid stratification. The aqueous phase was extracted twice with THF (600 mL), and the organic phases were combined and concentrated under reduced pressure (40-45° C.). The solid was slurried with pure water (2 mL/g) for 0.5 hour and filtered, and the filter cake was vacuum-dried for over 12 hours at 40° C. and P≤−0.1 MPa to obtain compound 1-2 as a pale-yellow solid.

$^1$H NMR (399 MHz, DMSO-$d_6$) δ=11.19 (s, 1H), 8.09 (d, J=8.2 Hz, 1H), 8.00 (d, J=1.6 Hz, 1H), 7.88 (dd, J=1.5, 8.3 Hz, 1H), 7.39 (dd, J=1.2, 2.0 Hz, 1H), 7.01 (d, J=2.0 Hz, 1H), 2.05 (s, 3H).

Step 15: Synthesis of the Compound Represented by Formula (I)

DMF (2.25 L) was added into a 5 L three-necked flask and stirred, then compound 1-2 (400.00 g) and HATU (744.83 g) were added successively and stirred for 30 min, followed by compound 1-SM2 (229.86 g). DIPEA (568.68 mL) was slowly added dropwise at room temperature within 1 hour. After addition, the reaction was further stirred at room temperature for 16 hours. Next, the reaction solution was transferred to a separatory funnel, ethyl acetate (2 L) and pure water (1 L) were added, and the solution was stirred for 2 min and then left standing for stratification to separate the water phase. Then pure water (1 L) was added to wash the water phase which was then stirred and allowed to stand for stratification. The combined aqueous phase was extracted three times with EtOAc (500 mL), and the organic phases were combined. The organic phase was washed twice with sodium carbonate solution (1.5 L), twice with potassium hydrogen sulfate solution (1 L) and twice with pure water (1 L), successively. The organic phase was concentrated under reduced pressure (40-45° C.) to obtain a crude product. Ethyl acetate (2 mL/g) was added to the crude product and the mixture was slurried for 1 hour. Finally, the slurried mixture was filtered and the filter cake was collected to obtain the compound represented by formula (I).

$^1$H NMR (400 MHz, DMSO-$d_6$) δ=11.13 (br s, 1H), 8.73 (br t, J=5.5 Hz, 1H), 8.05 (d, J=8.2 Hz, 1H), 7.83 (d, J=1.3 Hz, 1H), 7.74 (dd, J=1.5, 8.4 Hz, 1H), 7.36 (s, 1H), 6.98 (d, J=2.0 Hz, 1H), 3.71-3.48 (m, 5H), 3.45-3.31 (m, 1H), 3.45-3.30 (m, 1H), 3.27-3.21 (m, 1H), 3.14 (dd, J=9.9, 11.2 Hz, 1H), 2.03 (s, 3H), 1.53 (q, J=7.0 Hz, 2H).

Example 2 Preparation of Crystal Form a of Compound Represented by Formula (I)

35 mg of the compound represented by formula (I) and 400 μL of tert-butyl methyl ether were sequentially added into a 1.5 mL liquid phase vial, and thus ultrasonically mixed or dissolved. The suspension sample was stirred (protect from light) for 3 days on a constant temperature shaker (40° C.). Then the sample solution was centrifuged rapidly, and the centrifuged solid was dried in a vacuum drying oven at 30° C. for 5 hours. The obtained dry sample was subjected to XRPD, verifying that a crystal form A of compound represented by formula (I) was obtained.

Example 3 Preparation of Crystal Form B of Compound Represented by Formula (I)

35 mg of the compound represented by formula (I) and 400 μL of acetone were sequentially added into a 1.5 mL liquid phase vial, and thus ultrasonically mixed or dissolved. The suspension sample was stirred (protect from light) for 3 days on a constant temperature shaker (40° C.). Then the sample solution was subjected to rapid centrifugation, and the solid after centrifugation was dried in a vacuum drying oven at 30° C. for 5 hours. The obtained dry sample was subjected to XRPD, verifying that a crystal form B of compound represented by formula (I) was obtained.

Example 4 Pre-Stability Test of the Crystal Form B of Compound Represented by Formula (I)

TABLE 3

Research conditions and testing items

| Testing item | Condition | 0 day | 5 days | 10 days | 1 month |
|---|---|---|---|---|---|
| Influence factor test | High temperature (60° C., with the lid open) | X | X | X | — |
| | High humidity (Relative humidity 92.5%, with the lid open) | | X | X | — |
| | Light (total illuminance ≥ 1.2 × 10$^6$ Lux · hr/ near ultraviolet 200 w · hr/m$^2$, with the lid open) | | X (1 ICH) + light-proof | | |
| Accelerated test | 40° C./75%RH, with the lid open | X | — | X | X |
| | 60° C./75%RH, with the lid open | | — | X | X |

Note:
X indicates testing items, including: XRPD, content and related substances, day 0 samples were stored at −20° C.;
ICH indicate the illumination condition that guides the placement of the samples, i.e., illumination (total illuminance=1.2×10$^6$ Lux·hr/near ultraviolet=200 w·hr/m$^2$, with the lid open).

Experiment Steps:

About 10 mg of the crystal form B of the compound represented by formula (I) was weighed and placed at the bottom of a 40 mL glass bottle, and spread into a thin layer. The bottleneck was wrapped with aluminum foil paper (except for illuminated samples), and some small holes were punctured on the aluminum foil paper to ensure that the samples can fully contact the ambient air. The illuminated sample was placed at the bottom of a 40 mL glass bottle, which was placed vertically in the illuminated box with the lid open; the control sample was placed at the bottom of glass vials, which was placed vertically with the lid open, and wrapped with tin foil to protect it from light. Under each condition, 2 aliquots of sample were weighed in parallel at each time point, and an additional appropriate amount of sample (not weighed) was taken for XRPD detection. The prepared samples were placed under various conditions shown in the following Table, and samples were analyzed respectively by HPLC after reaching the time points. The analysis method is shown in Table 4, and the experimental results are shown in Table 5.

HPLC Analysis:

1.1 Preparation of Diluent and Mobile Phase

Diluent: Acetonitrile:Water (2:1)

Example: 1000 mL of acetonitrile and 500 mL of water were mixed evenly, ultrasonically degassed, and cooled to room temperature.

Mobile phase A: 0.1% trifluoroacetic acid aqueous solution

Example: 2.0 mL of trifluoroacetic acid was added to 2 L of water and mixed well, ultrasonically degassed, and cooled to room temperature.

Mobile phase B: 100% acetonitrile 1.2 Preparation of Control Sample and Sample Solutions The crystal form B of compound represented by formula (I) was used as control. The crystal form B of compound represented by formula (I) was placed in a glass bottle, then 5 mL of diluent was added into the bottle to a concentration of 1 mg/mL, and the solution was mix well ultrasonically. And then the mixture was diluted 5 times to obtain the control sample solution STD1. STD1 was diluted 1, 2, 4, 20 and 200 times to prepare a 1% control solution.

1.3 Preparation of Test Sample Solution

Diluent was added to each test sample to a concentration of 10 mL, then the samples were ultrasonically dissolved. HPLC test was performed after cooling to room temperature.

Meanwhile, the sample solution was diluted 5 times and mixed well, and then tested by HPLC. The analysis method is shown in Table 4.

TABLE 4

| HPLC analysis method | |
|---|---|
| Instrument | Agilent 1200 High Performance Liquid Chromatograph (PDS-PF-HPLC-16) |
| Column | Waters Xbridge shield RP18, 4.6 * 150 mm, 3.5 μm (PDS-HPLC-038) |
| Mobile phase A | 0.1% trifluoroacetic acid aqueous solution |
| Mobile phase B | 100% acetonitrile |
| Flow rate | 0.8 mL/min |
| Injection volume | 10 μL |
| Detection wavelength | 220 nm |
| Column temperature | 40° C. |
| Diluent | Acetonitrile: pure water 2/1 (v/v) |

| | duration (min) | Mobile phase A (%) | Mobile phase B (%) |
|---|---|---|---|
| Gradient elution program | 0.00 | 90 | 10 |
| | 50.00 | 10 | 90 |
| | 55.00 | 10 | 90 |
| | 57.00 | 90 | 10 |
| | 62.00 | 90 | 10 |

TABLE 5

HPLC analysis results of solid stability test of the crystal form B of the compound represented by formula (I)

| Relative retention time (min) | Day 0 | Illumination | Illumination of Control | 60° C., 5 days | 60° C., 10 days | 92.5% humidity, 5 days | 92.5% humidity, 10 days | 40° C., 75% humidity, 10 days | 40° C., 75%, humidity, 1 month | 60° C., 75% humidity, 10 days | 60° C., 75% humidity, 1 month |
|---|---|---|---|---|---|---|---|---|---|---|---|
| 0.16 | — | 0.07 | — | — | — | — | — | — | — | — | — |
| 0.19 | — | 0.32 | — | — | — | — | — | — | — | — | — |
| 0.24 | — | 0.12 | — | — | — | — | — | — | — | — | — |
| 0.26 | — | 0.12 | — | — | — | — | — | — | — | — | — |
| 0.31 | — | 0.12 | — | — | — | — | — | — | — | — | — |
| 0.36 | — | 0.19 | — | — | — | — | — | — | — | — | — |
| 0.38 | — | 0.08 | — | — | — | — | — | — | — | — | — |
| 0.60 | — | 0.28 | — | — | — | — | — | — | — | — | — |
| 0.62 | — | 0.12 | — | — | — | — | — | — | — | — | — |
| 0.70 | — | 0.10 | — | — | — | — | — | — | — | — | — |
| 0.78 | — | 0.16 | — | — | — | — | — | — | — | — | — |
| 0.79 | — | 0.24 | — | — | — | — | — | — | — | — | — |
| 0.82 | — | 2.26 | — | — | — | — | — | — | — | — | — |
| 0.87 | 0.35 | 4.49 | 0.34 | 0.35 | 0.36 | 0.36 | 0.35 | 0.34 | 0.34 | 0.35 | 0.35 |
| 0.89 | — | 0.07 | — | — | — | — | — | — | — | — | — |
| 0.90 | — | 0.07 | — | — | — | — | — | — | — | — | — |
| 1.07 | 0.06 | <0.05% | 0.07 | 0.07 | 0.07 | 0.07 | 0.06 | 0.06 | 0.07 | 0.07 | 0.07 |
| 1.12 | 0.65 | 0.52 | 0.64 | 0.65 | 0.65 | 0.65 | 0.65 | 0.65 | 0.65 | 0.65 | 0.65 |
| 1.14 | 0.14 | 0.12 | 0.13 | 0.13 | 0.13 | 0.13 | 0.13 | 0.13 | 0.13 | 0.13 | 0.13 |
| 1.42 | — | 0.06 | — | — | — | — | — | — | — | — | — |

TABLE 5-continued

HPLC analysis results of solid stability test of the crystal form B of the compound represented by formula (I)

| Relative retention time (min) | Day 0 | Illumination | Illumination of Control | 60° C., 5 days | 60° C., 10 days | 92.5% humidity, 5 days | 92.5% humidity, 10 days | 40° C., 75% humidity, 10 days | 40° C., 75% humidity, 1 month | 60° C., 75% humidity, 10 days | 60° C., 75% humidity, 1 month |
|---|---|---|---|---|---|---|---|---|---|---|---|
| TRS(%) | 1.20 | 9.50 | 1.18 | 1.19 | 1.21 | 1.21 | 1.20 | 1.19 | 1.20 | 1.20 | 1.21 |
| Assay (%) | 100.5 | 83.5 | 100.3 | 100.1 | 100.1 | 100.0 | 100.7 | 100.7 | 100.6 | 101.4 | 100.3 |

Note:
"-" means not detected;
TRS refers to the sum of the remaining impurities after removing the main peak;
Assay refers to the content of the sample.
Conclusion: The crystal form B of the compound represented by formula (I) is stable under high temperature and high humidity conditions.

Note: "-" means not detected;
TRS refers to the sum of the remaining impurities after removing the main peak;
Assay refers to the content of the sample.
Conclusion: The crystal form B of the compound represented by formula (I) is stable under high temperature and high humidity conditions.

Example 5 HBV In Vitro Test: Quantitative qPCR Test

1 Objectives of Experiment:
The HBV DNA content in HepG2.2.15 cells was detected by Real-time quantitative qPCR, and $EC_{50}$ value of compounds was used as an indicator to evaluate inhibitory effect of compounds on HBV.

2 Experimental Materials:
2.1 Cell Line: HepG2.2.15 Cells
HepG2.2.15 cell culture medium (DMEM/F12, Invitrogen-11330057; 10% serum, Invitrogen-10099141; 100 units/mL penicillin and 10 μg/mL streptomycin, Invitrogen-15140122; 1% non-essential amino acids, Invitrogen-11140076; 2 mM L-glutamine, Invitrogen-25030081; 300 μg/ml geneticin, Invitrogen-10131027

2.2 Reagents:
Pancreatin (Invitrogen-25300062)
DPBS (Hyclone-SH30028.01B)
DMSO (Sigma-D2650-100ML)
High-throughput DNA purification kit (QIAamp 96 DNA Blood Kit, Qiagen-51162)
Quantitative quick start universal probe reagent (FastStart Universal Probe Master, Roche-04914058001)

2.3 Consumables and Instruments:
96-well cell culture plate (Corning-3599)
$CO_2$ incubator (HERA-CELL-240)
Optical sealing film (ABI-4311971)
Quantitative PCR 96-well plate (Applied Biosystems-4306737)
Fluorescence quantitative PCR instrument (Applied Biosystems-7500 real time PCR system)

3. Experimental Steps and Methods:
3.1 HepG2.2.15 cells ($4 \times 10^4$ cells/well) were bedded to a 96-well plate and cultured overnight at 37° C., 5% $CO_2$.
3.2 On the day 2, the compound was diluted to a total of 8 concentrations, with a 3-fold gradient dilution. Different concentrations of compounds were added to the culture wells in duplicate. The final concentration of DMSO in the culture medium was 1%. 1 μM GLS4 was used as a 100% inhibition control; 1% DMSO was used as a 0% inhibition control.
3.3 On the day 5, the culture medium was replaced with fresh culture medium containing the compound.
3.4 On the day 8, the culture medium in the culture wells was collected, and DNA was extracted with the high-throughput DNA purification kit (Qiagen-51162). Refer product manual for specific steps.
3.5 The Preparation of PCR Reaction Solution is Shown in Table 6:

TABLE 6

Preparation of PCR reaction solution

| Item | Volume required for 1 well (μL) | Volume required for 80 wells (μL) |
|---|---|---|
| Quantitative quick start universal probe reagent | 12.5 | 1000 |
| Forward primer (10 μmol) | 1 | 80 |
| Reverse primer (10 μmol) | 1 | 80 |
| Probe (10 μmol) | 0.5 | 40 |

Forward primer sequence: GTGTCTGCGGCGTTT-TATCA (SEQ ID NO.1)
Reverse primer sequence: GACAAACGGGCAACAT-ACCTT (SEQ ID NO.2)
Probe sequence: 5'+FAM+CCTCTKCATCCTGCTGC-TATGCCTCATC(SEQ ID NO.3)+TAMRA-3'

3.6 15 μL of reaction mixture was added to each well of a 96-well PCR plate, and then 10 μL of sample DNA or HBV DNA standard was added to each well.
3.7 The reaction settings for PCR are: heating at 95° C. for 10 minutes; then denaturation at 95° C. for 15 seconds, and extension at 60° C. for 1 minute, a total of 40 cycles.
3.8 Data Analysis:
3.8.1 Calculation of the percentage of inhibition: % Inh.=[1−(number of DNA copies in the sample−number of 1 μM DNA copies in GLS4)/(number of DNA copies in the DMSO control−number of 1 μM DNA copies in GLS4)]× 100.
3.8.2 Calculation of $EC_{50}$: The 50% inhibitory concentration ($EC_{50}$) of the compound against HBV was calculated by GraphPad Prism software.
4. Results of the Experiment are Shown in Table 7:

TABLE 7

$EC_{50}$ test results of qPCR experiment

| Test compound | 50% inhibitory concentration ($EC_{50}$) value of HBV |
|---|---|
| Compound represented by formula (I) | 8.158 nM |

Conclusion: The compound represented by formula (I) has a significant inhibitory effect on HBV.

Example 6 Inhibition of Cytochrome P450 Isoenzymes

Objectives of experiment: To determine the inhibitory effect of the test compound on the activity of human liver microsomal cytochrome P450 isoenzymes (CYP1A2, CYP2C9, CYP2C19, CYP2D6 and CYP3A4).

Experimental operation: First, the test compound (10 mM) was diluted in a gradient to prepare the working solutions (100× final concentration). The concentrations of the working solutions were 5, 1.5, 0.5, 0.15, 0.05, 0.015 and 0.005 mM. Meanwhile, the working solutions of mixture (5 in 1) of positive inhibitors of each P450 isoenzyme (CYP1A2, CYP2C9, CYP2C19, CYP2D6 and CYP3A4) and the specific substrate of the isoenzymes were also prepared; the human liver microsomes frozen in the refrigerator at −80° C. were unfrozen on ice. After the human liver microsomes were completely dissolved, they were diluted with PB to prepare a certain concentration (0.253 mg/mL) of working solution; 20 uL of the substrate mixture was added into the reaction plate (20 μl PB was added into the Blank well) as well as 158 μL of human liver microsome working solution, then the reaction plate was placed on ice and set aside; at this time, 2 μL of each concentration of test compound (N=1) and specific inhibitor (N=2) were added to the corresponding well, the group without inhibitor (test compound or positive inhibitor) was added with the corresponding organic solvent as a control sample (the test compound control sample was 1:1 DMSO:MeOH, and the positive control sample was 1:9 DMSO:MeOH); after pre-incubating in a 37° C. water bath for 10 min, the reaction plate was added with 20 μL of coenzyme factor (NADPH) solution and water bathed at 37° C. for 10 min; 400 μL of cold acetonitrile solution (internal standard was 200 ng/mL Tolbutamide and Labetalol) was added to terminate the reaction; the reaction plate was then placed on a shaker and shaken for 10 min, followed by centrifuging at 4,000 rpm for 20 min; 200 μL of supernatant was added to 100 μL of water for sample dilution; finally, the plate was sealed, shaken well, and subjected to LC/MS/MS detection. The experimental results are shown in Table 8:

TABLE 8

Results of inhibitory effect of test compound on the activity of human liver microsomal cytochrome P450 isoenzymes IC50 (μM)

| Compound | CYP1A2 | CYP2C9 | CYP2C19 | CYP2D6 | CYP3A4 |
|---|---|---|---|---|---|
| The compound represented by formula (I) | >50 | >50 | >50 | >50 | >50 |

Conclusion: the compound represented by formula (I) has no evident inhibitory effect on CYP1A2, CYP2C9, CYP2C19, CYP2D6 and CYP3A4.

Example 7 Study on Plasma Protein Binding Rate

Objectives of Experiment: to determine the binding rate of test compound to proteins in human and CD-1 mouse plasma Experimental operation: 796 μL of blank plasma was taken from human and CD-1 mouse, and 4 μL of test compound working solution (400 μM) or warfarin working solution (400 μM) was added to make the final concentrations of both test compound and warfarin in the plasma sample 2 μM. The sample was mixed thoroughly. The final concentration of DMSO in the organic phase was 0.5%; 50 μt of plasma samples of test compound and warfarin was pipetted into the sample receiving plate (in triplicate), and immediately the corresponding volume of blank plasma or buffer was added to make the final volume of each sample 100 μL and the volume ratio of plasma:dialysis buffer 1:1. Then 400 μL of stop solution is added to these samples. These samples would be used as TO samples for determination of recovery and stability. The TO samples were stored at 2-8° C. and waited for subsequent processing with other dialyzed samples; 150 μL of the test samples of compound and warfarin plasma were added to the dosing end of each dialysis wells, and 150 μL of blank dialysis buffer to the receiving end of the corresponding dialysis wells. Then, the dialysis plate was sealed with a gas-permeable membrane and incubated in a humidified incubator at 5% $CO_2$ and 37° C. with shaking at about 100 rpm for 4 hours. After the dialysis, 50 μL of the dialysis buffer sample and the dialysis plasma sample were pipetted into a new sample receiving plate. Corresponding volume of blank plasma or buffer was added to the samples, so that the final volume of each sample well was 100 μL, and the volume ratio of plasma:dialysis buffer was 1:1. All samples were analyzed by LC/MS/MS after protein precipitation, and the protein binding rate and recovery rate was calculated with the formula: % Unbound (unbound rate)=100*FC/TC, % Bound (bound rate)=100-% Unbound, % Recovery (recovery rate)=100*(FC+TC)/T0. Results of the experiment are shown in Table 9:

TABLE 9

The binding rate of test compound to protein in human and CD-1 mouse plasma

| Compound | Binding rate of plasma protein | |
|---|---|---|
| | Human (Homo sapiens) | CD-1 mouse (mus musculus) |
| The compound represented by formula (I) | 81% | 94% |

Conclusion: the compound represented by formula (1) shows lower binding rate to proteins in both human and CD-1 mouse plasma.

Example 8 In Vivo Pharmacokinetic Study

1. Study on the Pharmacokinetics of Oral Administration and Intravenous Injection of the Compound Represented by Formula (I) in Balb/c Mice The compound represented by formula (I) was mixed with 5% DMSO/55% polyethylene glycol 400/40% aqueous solution, vortexed and sonicated to obtain an approximately clear solution of 1 mg/mL, which was then filtered by a microporous membrane for later use. Female Balb/c mice aged 7 to 10 weeks were selected and the candidate compound solution was administered intravenously at a dose of 1 mg/kg. The compound represented by formula (I) was mixed with 10% solutol (polyethylene glycol-15 hydroxystearate) aqueous solution, vortexed and sonicated to obtain an approximately clear solution of 1 mg/mL, which was then filtered through a microporous membrane for later use. Female Balb/c mice aged 7 to 10 weeks were selected and the candidate compound solution was orally administered at a dose of 10 mg/kg.

Whole blood was collected at a certain period of time to prepare plasma, drug concentration was analyzed by LC-MS/MS method, and pharmacokinetic parameters was calculated by Phoenix WinNonlin software (Pharsight, USA).

2. Study on the Pharmacokinetics of Oral Administration and Intravenous Injection of the Compound Represented by Formula (I) in SD Rats The compound represented by formula (I) was mixed with 5% DMSO/55% polyethylene glycol 400/40% aqueous solution, vortexed and sonicated to obtain an approximately clear solution of 1 mg/mL, which was then filtered by a microporous membrane for later use. Male SD rats aged 7 to 10 weeks were selected and the candidate compound solution was administered intravenously at a dose of 1 mg/kg.

The compound represented by formula (I) was mixed with 10% solutol aqueous solution, vortexed and sonicated to obtain an approximately clear solution of 1 mg/mL, which was then filtered through a microporous membrane for later use. Male SD rats aged 7 to 10 weeks were selected and the candidate compound solution was orally administered at a dose of 10 mg/kg.

Whole blood was collected at a certain period of time to prepare plasma, drug concentration was analyzed by LC-MS/MS method, and pharmacokinetic parameters was calculated by Phoenix WinNonlin software (Pharsight, USA).

3. Study on the Pharmacokinetics of Oral Administration and Intravenous Injection of the Compound Represented by Formula (I) in Beagle The compound represented by formula (I) was mixed with 5% DMSO/55% polyethylene glycol 400/40% aqueous solution, vortexed and sonicated to obtain an approximately clear solution of 1 mg/mL, which was then filtered by a microporous membrane for later use. Male beagle dogs weighed about 10 kg were selected and the candidate compound solution was administered intravenously at a dose of 1 mg/kg.

The compound represented by formula (I) was mixed with 10% solutol aqueous solution, vortexed and sonicated to obtain an approximately clear solution of 2 mg/mL, which was then filtered through a microporous membrane for later use. Male beagle dogs weighed about 10 kg were selected and the candidate compound solution was orally administered at a dose of 10 mg/kg.

Whole blood was collected at a certain period of time to prepare plasma, drug concentration was analyzed by LC-MS/MS method, and pharmacokinetic parameters was calculated by Phoenix WinNonlin software (Pharsight, USA).

The experimental results are shown in Table 10:

TABLE 10

Results of pharmacokinetic of test compound

|  |  |  | The compound represented by formula (I) | | |
| --- | --- | --- | --- | --- | --- |
|  | Compound |  | Mice | Rats | Dogs |
| PK | iv | $T_{1/2}$ (h) | 1.2 | 0.95 | 2.87 |
|  | (1 mpk) | $Vd_{ss}$ (L/kg) | 0.45 | 0.56 | 2.95 |
|  |  | Cl (ml/min/kg) | 8.5 | 8.5 | 15.6 |
|  |  | $AUC_{0-last}$ (nM · h) | 4672 | 4818 | 2679 |
|  | po | $T_{max}$ (h) | 0.5 | 0.5 | 1.67 |
|  | (10 mpk) | $C_{max}$ (nM) | 19933 | 8573 | 5847 |
|  |  | $AUC_{0-24h}$ (nM · h) | 32543 | 31132 | 33218 |
|  |  | F % | 70 | 65 | 126 |

Note: $T_{1/2}$ means half-life; $Vd_{ss}$ means apparent volume of distribution; Cl means clearance rate; $AUC_{0\_last}$ means area below the drug-time curve; $T_{max}$ means peak time; $C_{max}$ means peak concentration; F % means oral bioavailability; iv means intravenous injection; PO means oral administration; mpk means mg/kg.

Conclusion: the compound represented by formula (I) has a good single or partial index of pharmacokinetics in Beagle.

Example 9 Study on In Vivo Drug Efficacy

AAV/HBV Model

Objectives of Experiment: to detect the anti-hepatitis B virus effect of the compound in vivo using the AAV/HBV mouse model.

Figure 7:
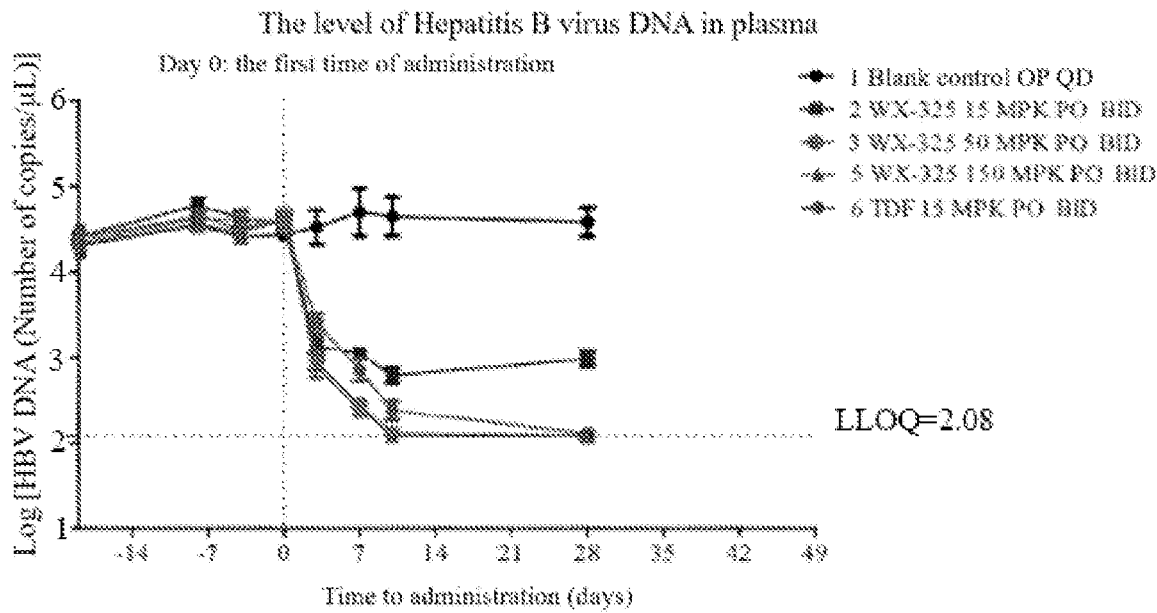
FIG. 7: The level of Hepatitis B virus DNA in plasma; broken line 1 means blank control, 10% solutol aqueous solution was administered quaque die (QD), per os (PO); broken line 2 means that WX-325 was administered at a dose of 15 mg/kg bis in die (BID) at an interval of 8 hours, per os (PO); the broken line 3 means that WX-325 was administered at a dose of 50 mg/kg bis in die (BID) at an interval of 8 hours, per os (PO); broken line 5 means that WX-325 was administered at a dose of 150 mg/kg bis in die (BID) at an interval of 8 hours, per os (PO); broken line 6 means that tenofovir (TDF) of the positive compound was administered at a dose of 15 mg/kg bis in die (BID) at an interval of 8 hours, per os (PO); LLOQ means lower limit of detection; Note: WX-325 in FIG. 7 means the compound represented by formula (I) of the present invention.
Figure 8:
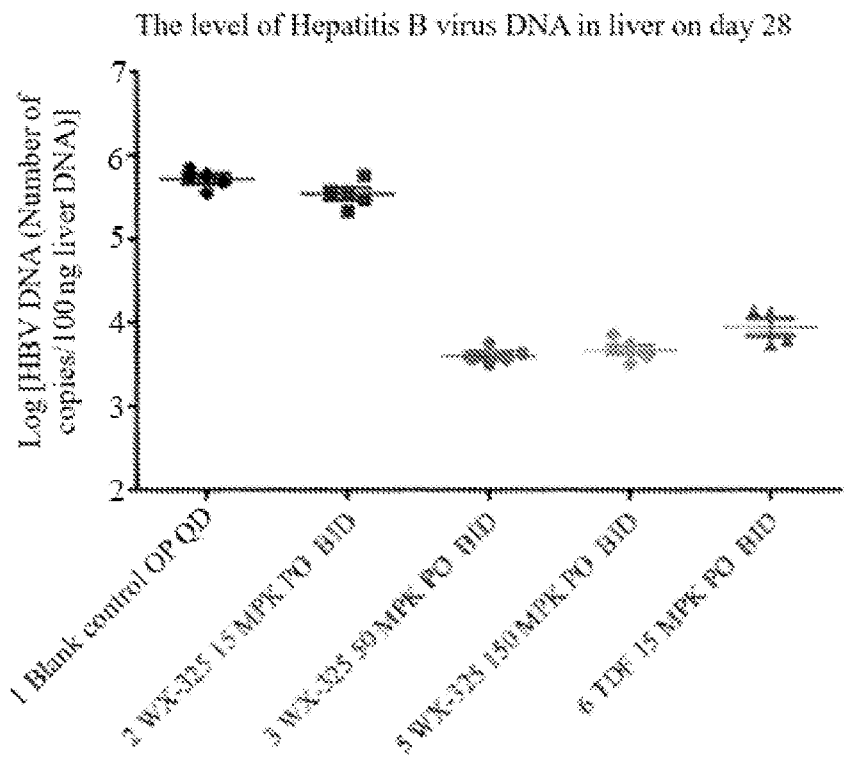
FIG. 8: The level of hepatitis B virus DNA in the liver on the day 28; Note: QD means quaque die; BID means bis in die; MPK means mg/kg; Vehicle means blank control; Note: WX-325 in FIG. 8 Means the compound represented by formula (I) of the present invention.

Experimental operation: The day of the first administration was designated as day 0, the day before administration was designated as day −1, the day after administration was designated as day 1, and so on. On the day 28 before administration, all animals were tail intravenously injected with $1*10^{11}$ v.g. rAAV8-1.3HBV virus, 200 μL for each animal. 14 days prior to administration and 7 days prior to administration, blood serum were collected from all mice injected with rAAV8-1.3HBV virus through submandibular vein. The collected blood samples were placed at 37° C. for about 30 minutes, then centrifuged at 13,200 g at 4° C. for 3 minutes, and the supernatant was collected. The content of HBV DNA, HBeAg and HBsAg were detected using the serum. Mice with lower levels of HBV DNA, HBsAg and HBeAg and lighter weight would likely be excluded from the experiment. The selected 25 mice were equally assigned to each group, and it was ensured that there was no statistical difference in HBV DNA, HBsAg and HBeAg levels and body weight of mice in each compound treatment group on the day 21 after virus injection compared to those of the solvent group (P>0.05). The compound represented by formula (I) (WX-325) was mixed with 10% solutol aqueous solution, vortexed and sonicated to obtain a homogeneous suspension, which was filtered by a microporous membrane for later use. Tenofovir, as a positive compound, was dissolved in physiological saline, sonicated and stirred until dissolved, then prepared as a 0.1 mg/mL master mix, which was diluted to 0.01 mg/ml with physiological saline, and stored at 4° C. until use. The compound represented by formula (I) (WX-325) was administered per os (PO) and bis in die (BID), at an interval of 8 hours. The reference compound tenofovir was administered per os and bis in die. Both drugs were administered for 28 days, and blood samples were taken on day 3, 7, 10 and 28 after administration, and the level of HBV DNA in plasma was detected by qPCR. On day 28, the mice were euthanized by $CO_2$ inhalation, their livers were collected, and the level of HBV DNA was measured by qPCR. The experiment results are shown in FIG. 7 and FIG. 8.

Conclusion: the compound of the present invention shows a good in vivo efficacy and a dose-dependent effect.

It is to be understood for those skilled in the art that the foregoing description of specific embodiments is intended to be purely illustrative, and various changes or modifications will be apparent to those skilled in the art without departing from the principle and essence of the present invention. Therefore, the present invention is not intended to be limited other than expressly set forth in the appended claims.

What is claimed is:

1. A crystal form A of a compound represented by formula (I) having an X-ray powder diffraction (XRPD) pattern comprising characteristic diffraction peaks with the following angles of 2θ: 5.56±0.2°, 15.56±0.2° and 16.17±0.2°,

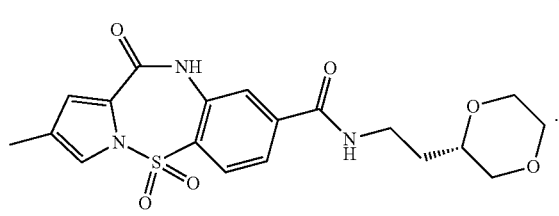

(I)

2. The crystal form A of claim 1, wherein the X-ray powder diffraction pattern comprises characteristic diffraction peaks with the following angles of 2θ: 5.56±0.2°, 10.84±0.2°, 15.56±0.2°, 16.17±0.2°, 22.14±0.2°, 22.70±0.2°, 27.76±0.2° and 28.44±0.2°.

3. The crystal form A of claim 2, wherein the XRPD pattern is shown in FIG. 1.

4. The crystal form A of claim 1 exhibiting an endothermic peak with an onset of 229.95° C. as measured by differential scanning calorimetry curve (DSC).

Figure 2:
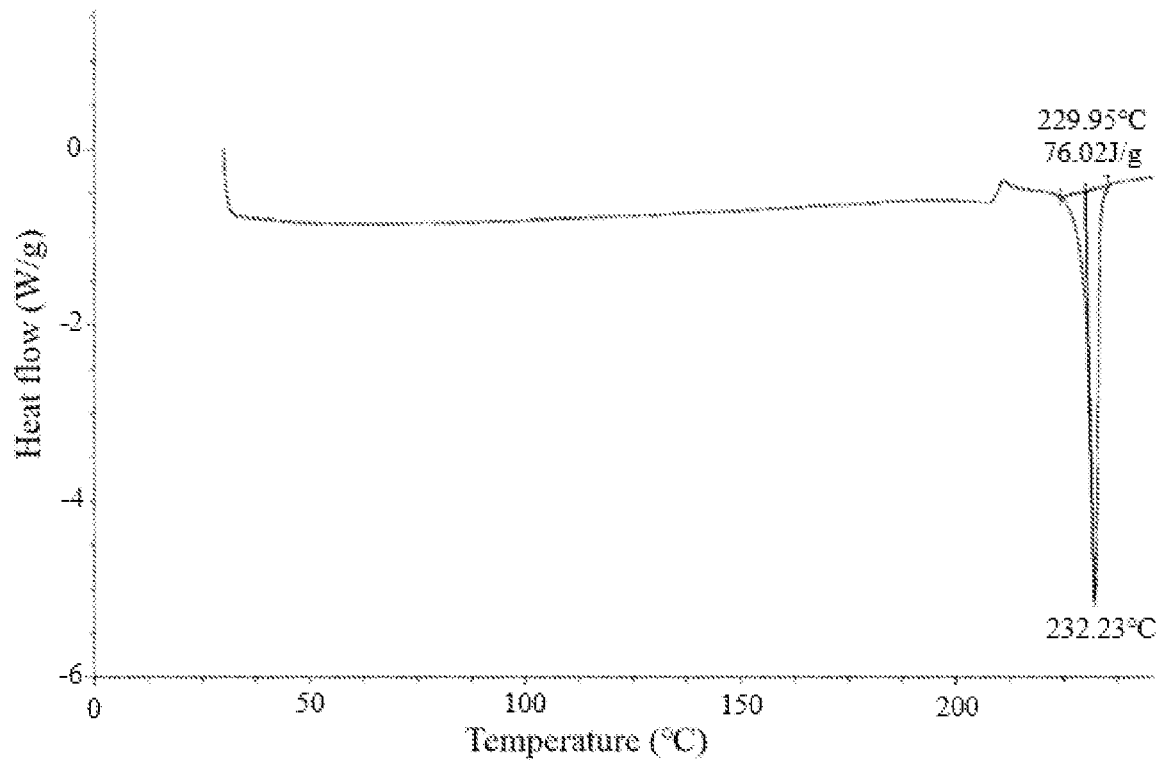
FIG. 2 is the DSC pattern of the crystal form A of the compound represented by formula (I).

5. The crystal form A of claim 4, wherein the DSC is shown in FIG. 2.

6. The crystal form A of claim 1 having a thermogravimetric analysis (TGA) curve with a weight loss of 0.3382% at 62±3° C. and a weight loss of 0.8753% at 230±3° C.

Figure 3:
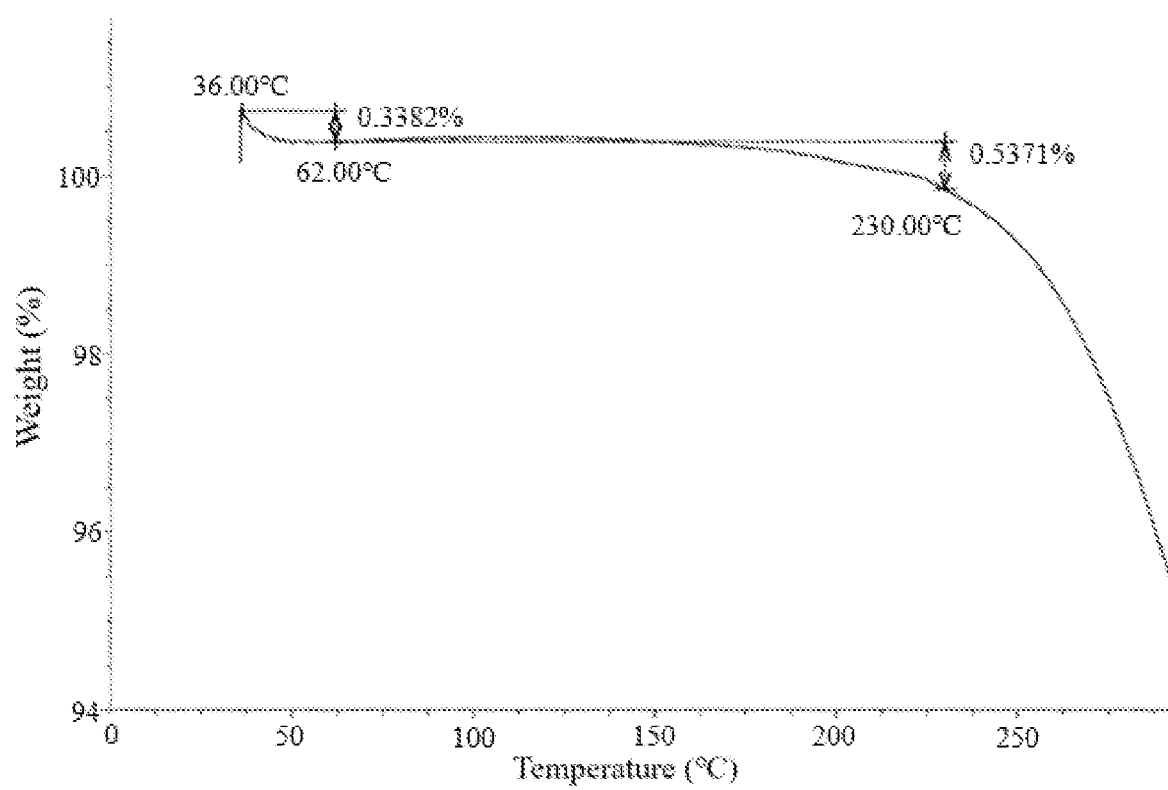
FIG. 3 is the TGA pattern of the crystal form A of the compound represented by formula (I).

7. The crystal form A of claim 6, wherein the TGA is shown in FIG. 3.

8. A crystal form B of a compound represented by formula (I) having an X-ray powder diffraction pattern comprising characteristic diffraction peaks with the following angles of 2θ: 12.70±0.2°, 15.64±0.2° and 23.03±0.2°,

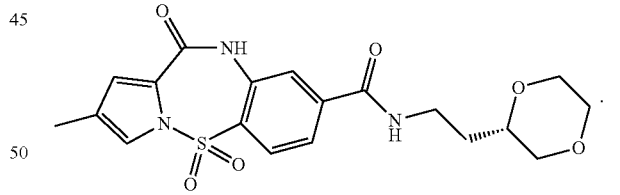

(I)

9. The crystal form B of claim 8, wherein the X-ray powder diffraction pattern comprises characteristic diffraction peaks with the following angles of 2θ: 9.56±0.2°, 12.70±0.2°, 14.41±0.2°, 15.64±0.2°, 19.70±0.2°, 23.03±0.2°, 23.98±0.2° and 27.65±0.2°.

Figure 4:
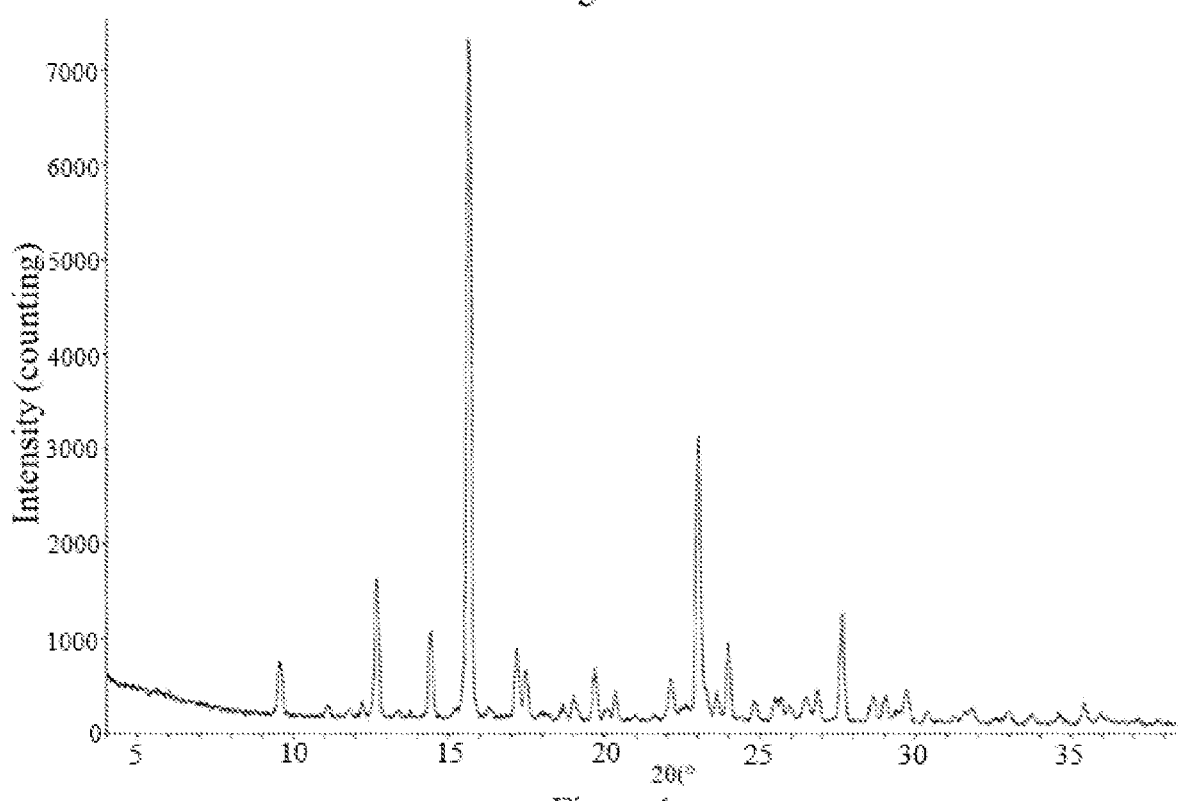
FIG. 4 is the XRPD pattern of Cu-Kα radiation of the crystal form B of the compound represented by formula (I).

10. The crystal form B of claim 9, wherein the XRPD pattern is shown in FIG. 4.

11. The crystal form B of claim 8 exhibiting an endothermic peak with an onset of 233.59° C. as measured by differential scanning calorimetry curve.

Figure 5:
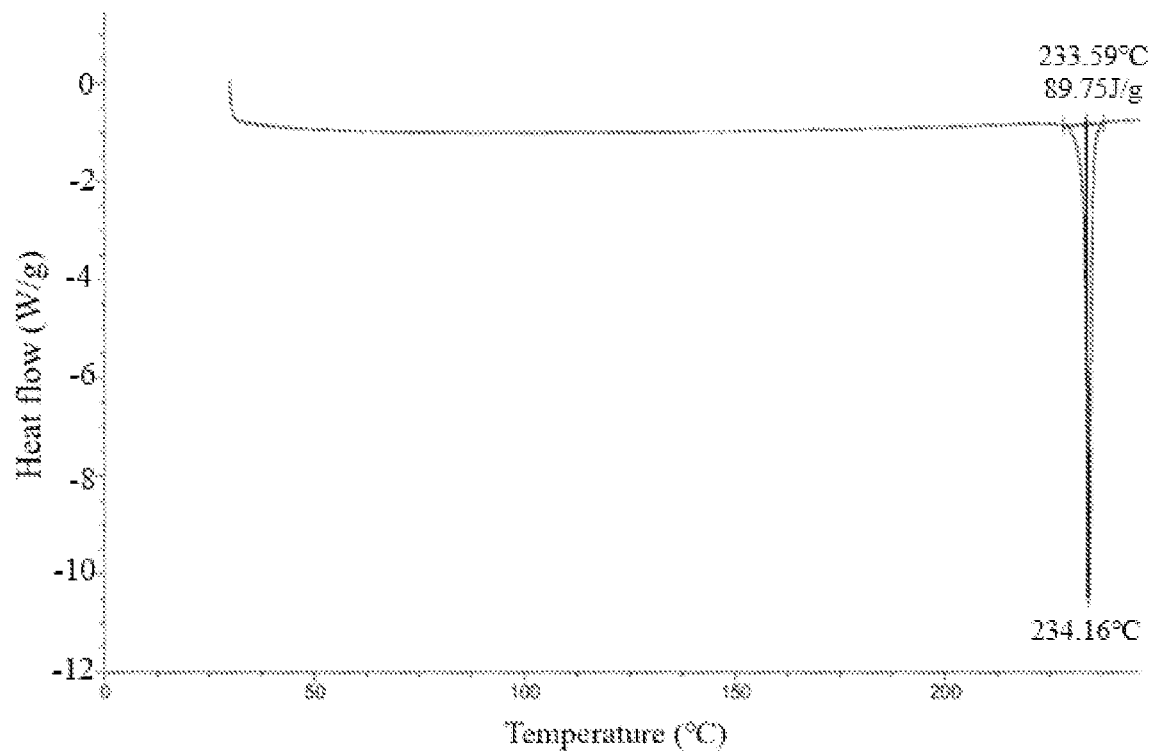
FIG. 5 is the DSC pattern of the crystal form B of the compound represented by formula (I).

12. The crystal form B of claim 11, wherein the DSC is shown in FIG. 5.

13. The crystal form B of claim 8 having a thermogravimetric analysis curve with a weight loss of 0.04890% at 120±3° C.

Figure 6:
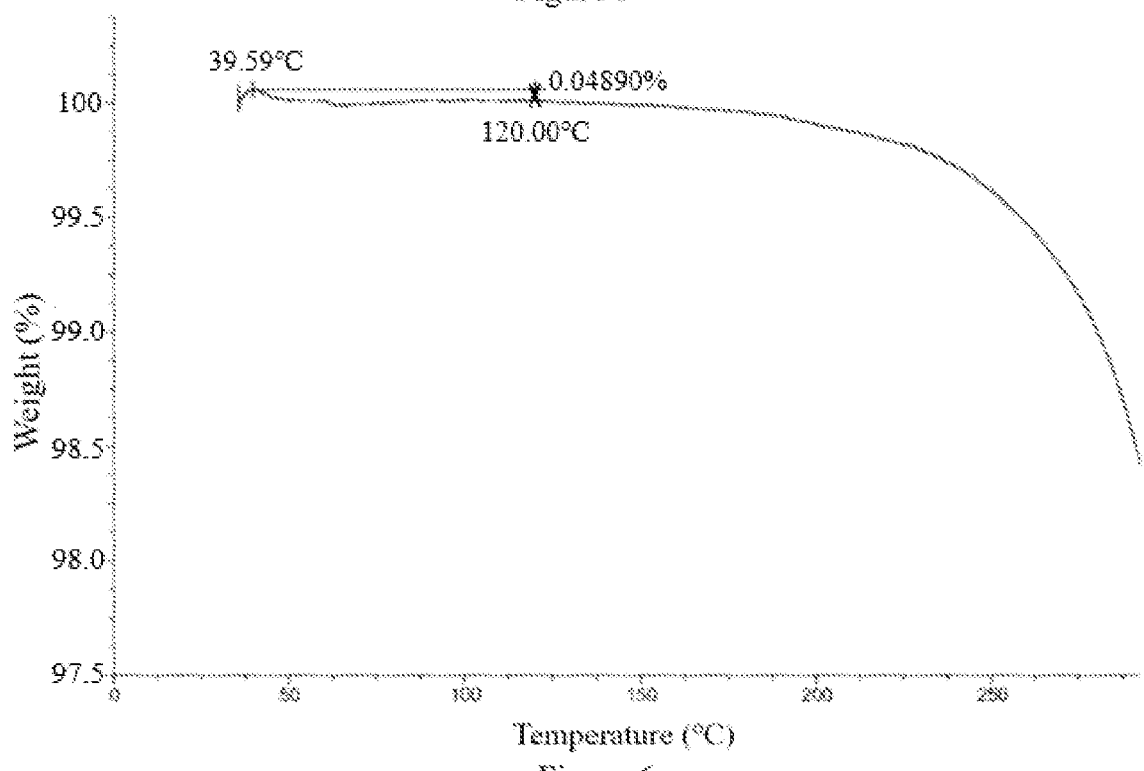
FIG. 6 is the TGA pattern of the crystal form B of the compound represented by formula (I).

14. The crystal form B of claim 13, wherein the TGA is shown in FIG. 6.

15. A method for treating hepatitis B in a subject in need thereof, comprising administering an effective amount of the crystal form A of claim 1 to the subject.

16. A method for treating hepatitis B in a subject in need thereof, comprising administering an effective amount of the crystal form B of claim 8 to the subject.

* * * * *